(12) United States Patent
Meyer

(10) Patent No.: US 6,925,886 B2
(45) Date of Patent: Aug. 9, 2005

(54) DENTAL TREATMENT ROOM VACUUM FLOW MEASUREMENT DEVICE

(75) Inventor: James Isaac Meyer, Spearfish, SD (US)

(73) Assignee: RAMVAC Dental Products, Inc., Spearfish, SD (US)

( * ) Notice: Subject to any disclaimer, the term of this patent is extended or adjusted under 35 U.S.C. 154(b) by 36 days.

(21) Appl. No.: 10/385,429

(22) Filed: Mar. 12, 2003

(65) Prior Publication Data

US 2004/0177698 A1 Sep. 16, 2004

(51) Int. Cl.$^7$ ................................................ G01L 7/04
(52) U.S. Cl. ........................ 73/732; 73/1.16; 73/1.32
(58) Field of Search ..................... 73/700–756, 1.16, 73/1.35, 195

(56) References Cited

U.S. PATENT DOCUMENTS

| | | | |
|---|---|---|---|
| 4,894,145 A | 1/1990 | Jensen | |
| 5,058,601 A | * 10/1991 | Riker | ........................ 600/538 |
| 5,407,465 A | 4/1995 | Schaub et al. | |
| 5,485,754 A | 1/1996 | Harpster | |
| 5,637,809 A | 6/1997 | Traina et al. | |
| 5,752,411 A | 5/1998 | Harpster | |
| 6,325,624 B1 | * 12/2001 | Kutsch et al. | ................ 433/88 |
| 6,347,649 B1 | 2/2002 | Pope et al. | |
| 6,406,294 B1 | * 6/2002 | Bell | ............................ 433/33 |

* cited by examiner

Primary Examiner—Edward Lefkowitz
Assistant Examiner—Jermaine Jenkins
(74) Attorney, Agent, or Firm—Nixon & Vanderhye P.C.

(57) ABSTRACT

A vacuum flow measurement device measures the quantity of air flowing into a high-volume evacuator (HVE) vacuum tip commonly found in dental treatment rooms. The device includes a tubular member constructed to mimic internal structural characteristics of a HVE tip. The tubular member includes a valve end coupleable with a HVE valve and an open end. A pressure gauge is connected to the tubular member via a port spaced from the open end of the tubular member. When the vacuum flow measurement device is coupled with the HVE valve, an air flow rate is determined as a function of pressure measured via the pressure gauge.

8 Claims, 2 Drawing Sheets

DENTAL TREATMENT ROOM VACUUM FLOW MEASUREMENT DEVICE

CROSS-REFERENCES TO RELATED APPLICATIONS (NOT APPLICABLE)

STATEMENT REGARDING FEDERALLY SPONSORED RESEARCH OR DEVELOPMENT (NOT APPLICABLE)

BACKGROUND OF THE INVENTION

The present invention relates to a dental treatment room vacuum flow measurement device and, more particularly, to a device designed to measure the quantity of air flowing into a high-volume evacuator (HVE) vacuum tip commonly found in dental treatment rooms.

Dental treatment rooms require a vacuum pump for driving vacuum air flow through a HVE vacuum tip. Such a tip is typically placed in a dental patient's mouth to remove fluid and debris from the patient's mouth during a dental treatment.

It is desirable to measure the performance of a vacuum pump generating the vacuum air flow at the HVE tip. Conventional measuring devices, however, add flow restriction to the system, therefore modifying the system that is measured and introducing error into the measurement.

BRIEF SUMMARY OF THE INVENTION

It is thus an object of the invention to provide a device designed to measure the quantity of air flowing into a HVE vacuum tip accurately and reliably. Generally, the device includes a tube that is similar in size and shape to that of a HVE tip and a pressure gauge. To measure air flow, the HVE tip is replaced with the device. The pressure-flow characteristics of the device are designed to closely match the pressure-flow characteristics of a HVE tip, minimizing the effect on system performance of replacing the HVE tip with the flow measurement device.

In an exemplary embodiment of the invention, a vacuum flow measurement device includes a tubular member constructed to mimic internal structural characteristics of a high-volume evacuator (HVE) tip. The tubular member has a valve end coupleable with a HVE valve and an open end. A pressure gauge is connected to the tubular member via a port spaced from the open end of the tubular member. When the vacuum flow measurement device is coupled with the HVE valve, an airflow rate is determined as a function of pressure measured via the pressure gauge. The device may further include a chart representing the airflow rate as a function of pressure.

In another exemplary embodiment of the invention, a method of measuring vacuum flow uses the flow measurement device of the invention. The method includes the step of (a) attaching a valve end of the tubular member to a HVE valve; (b) reading a pressure value from the pressure gauge; and (c) determining the vacuum flow airflow rate based on the pressure value read in step (b). In this context, the method may further include the step of (d) preparing a chart showing airflow rate as a function of pressure, where step (c) is practiced by referring to the chart. In one preferred embodiment, step (d) is practiced by attaching the flow measurement device to a peripheral airflow system having a known airflow rate; reading a first pressure value from the pressure gauge and plotting the airflow rate versus the first pressure; modifying the airflow rate of the peripheral airflow system; reading a second pressure value from the pressure gauge and plotting the airflow rate versus the second pressure; and repeating the modifying and reading steps as necessary and generating the chart based on plotted values.

In still another exemplary embodiment of the invention, a method of determining a vacuum airflow rate in a dental vacuum system includes the steps of replacing a high-volume evacuator (HVE) tip with a vacuum flow measurement device; measuring a pressure drop through the vacuum flow measurement device; and determining the vacuum airflow rate based on the pressure drop in the vacuum flow measurement device. The method may further include, prior to the replacing step, the step of providing the vacuum flow measurement device with pressure-flow characteristics that substantially match pressure-flow characteristics of the HVE tip.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Figure 1:
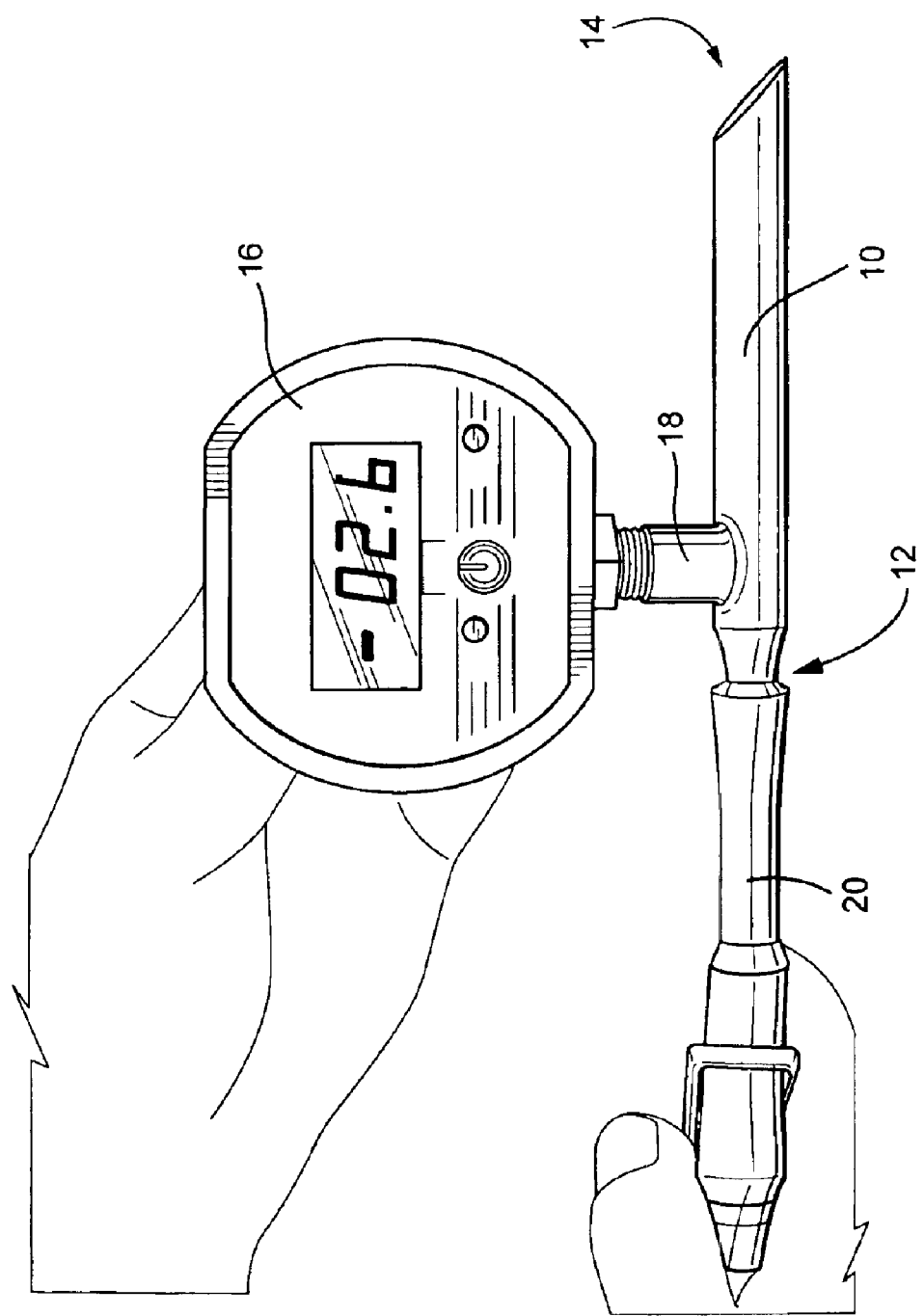
FIG. 1 illustrates the device according to the present invention.

With reference to FIG. 1, the device according to the present invention includes a tubular member 10 constructed to mimic internal structural characteristics of a HVE tip. In particular, the tubular member 10 is generally similar in size and shape to that of the HVE tip, including overall length, internal diameter, shape of tip, etc. The tubular member has a valve end 12 coupleable with a HVE valve 20 and an open end 14 at an opposite end thereof. As shown in FIG. 1, the open end 14 is angled at its opening to further reflect the pressure-flow characteristics of a HVE tip. In a preferred embodiment, the tubular member 10 is formed of a machined steel tube.

A pressure gauge 16 is connected to the tubular member 10 via a port 18 spaced from the open end 14 of the tubular member 10. The pressure gauge 16 is typically of known construction, and the operational details thereof will not be further described. One suitable pressure gauge is the SDPGB-30I+100PG5 manufactured by Honeywell, although many other pressure gauges may also be suitable, and the invention is not meant to be limited to the described example. A port 18 is preferably approximately 3½ inches from the open end 14 of the tubular member 10, although other distances may be suitable. The port 18 may be fixed to the tubular member 10 by any suitable means, an example of which is by welding.

Figure 2:
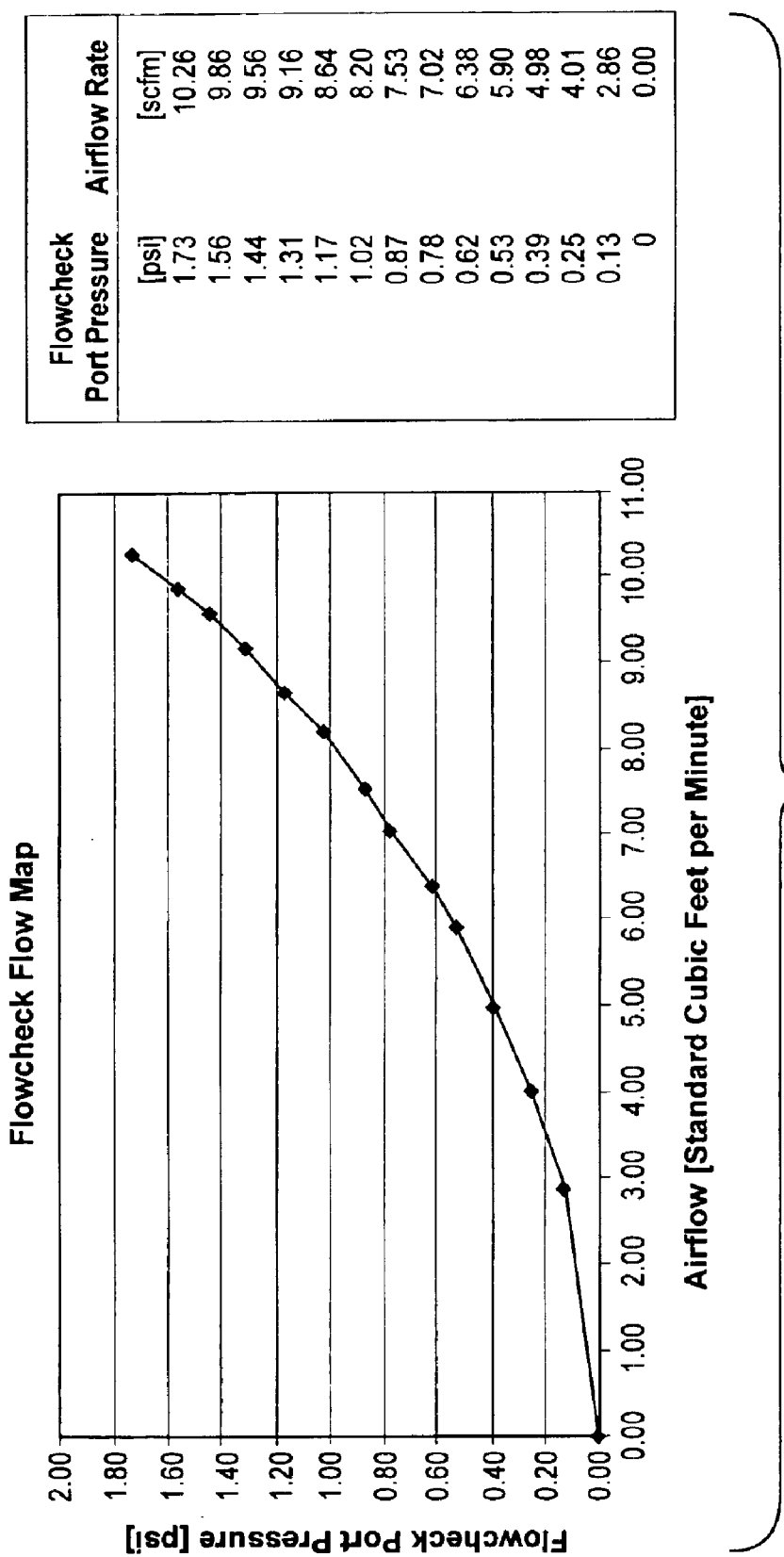
FIG. 2 is an exemplary chart representing air flow rate as a function of pressure.

When the vacuum flow measurement device shown in FIG. 1 is coupled with the HVE valve 20, an air flow rate can be determined as a function of the pressure measured via the pressure gauge 16. The air flow rate can be determined by formula via a component of Bernoulli's law and other factors or preferably by experimentation and interpolation. FIG. 2 is an exemplary graph representing air flow rate as a function of pressure. The graph is prepared by experimentally generating points on the graph and interpolating to determine the curve shown in FIG. 2. In this context, to generate the chart, the flow measurement device of the present invention is attached to a peripheral air flow system having a known air flow rate. A first pressure value is then read from the pressure gauge 16, and the air flow rate versus the first pressure is plotted on the graph. Subsequently, the known air flow rate is modified, and a second pressure value from the pressure gauge 16 is read, and the air flow rate is plotted versus the second pressure. The steps are repeated as necessary, and the chart generated based on the plotted values. In the exemplary chart of FIG. 2, fourteen different pressure values are plotted against the known air flow rates, and the air flow curve is filled in.

In order to evaluate the performance of the vacuum pump, the HVE vacuum tip is removed from the HVE valve 20, and the vacuum flow measurement device of the present invention is connected to the HVE valve 20. When air is flowing through the tube 10, there will be a pressure drop from atmospheric pressure to the pressure measured by the pressure gauge 16. As noted, the pressure drop is a function of air flow rate. After reading the pressure on the pressure gauge 16, the user can consult the chart such as the exemplary chart shown in FIG. 2 representing the air flow rate as a function of pressure.

With the structure of the present invention, the pressure-flow characteristics of the device are designed to closely match the pressure-flow characteristics of a HVE tip. This construction minimizes the effect on system performance of replacing the HVE tip with the flow measurement device. The device is easy and inexpensive to manufacture while providing reliable and accurate results.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A vacuum flow measurement device for measuring vacuum flow of a vacuum system having a high-volume evacuator (HVE) tip, the vacuum flow measurement device comprising:
   a tubular member constructed to mimic internal structural characteristics of the HVE tip, the tubular member replacing the vacuum system HVE tip and having a valve end coupleable with a HVE valve of the vacuum system and an open end; and
   a pressure gauge connected to the tubular member via a port spaced from the open end of the tubular member, wherein the device is constructed such that a vacuum flow airflow rate of the vacuum system is determined based on a pressure reading from the pressure gauge when the valve end is coupled with the HVE valve.

2. A vacuum flow measurement device according to claim 1, wherein when the vacuum flow measurement device is coupled with the HVE valve, an airflow rate is determined as a function of pressure measured via the pressure gauge.

3. A vacuum flow measurement device according to claim 2, further comprising a chart representing the airflow rate as a function of pressure.

4. A method of measuring vacuum flow of a vacuum system having a high-volume evacuator (HVE) tip using a flow measurement device including a tubular member constructed to mimic internal structural characteristics of the HVE tip, and a pressure gauge connected to the tubular member, the method comprising:
   (a) removing the vacuum system HVE tip and attaching a valve end of the tubular member to a HVE valve of the vacuum system;
   (b) reading a pressure value from the pressure gauge; and
   (c) determining the vacuum flow airflow rate of the vacuum system based on the pressure value read in step (b).

5. A method according to claim 4, further comprising, (d) preparing a chart showing airflow rate as a function of pressure, wherein step (c) is practiced by referring to the chart.

6. A method according to claim 5, wherein step (d) is practiced by:
   attaching the flow measurement device to a peripheral airflow system having a known airflow rate;
   reading a first pressure value from the pressure gauge and plotting the airflow rate versus the first pressure;
   modifying the airflow rate of the peripheral airflow system;
   reading a second pressure value from the pressure gauge and plotting the airflow rate versus the second pressure; and
   repeating the modifying and reading steps as necessary and generating the chart based on plotted values.

7. A method of determining a vacuum airflow rate in a dental vacuum system, the method comprising replacing a high-volume evacuator (HVE) tip with a vacuum flow measurement device, measuring a pressure drop through the vacuum flow measurement device; and determining the vacuum airflow rate based on the pressure drop in the vacuum flow measurement device.

8. A method according to claim 7, comprising, prior to the replacing step, the step of providing the vacuum flow measurement device with pressure-flow characteristics that substantially match pressure-flow characteristics of the HVE tip.

* * * * *